United States Patent
Cao et al.

(10) Patent No.: US 10,751,371 B2
(45) Date of Patent: Aug. 25, 2020

(54) USE OF ALLOGENEIC INTERSTITIAL VESSEL-LAYER CELL AND ALLOGENEIC MESENCHYMAL PROGENITOR CELL FOR PREVENTING OR TREATING OSTEOARTHRITIS

(71) Applicants: CELLULAR BIOMEDICINE GROUP (SHANGHAI) LTD., Shanghai (CN); CELLULAR BIOMEDICINE GROUP (WUXI) LTD., Jiangsu (CN)

(72) Inventors: Wei Cao, Shanghai (CN); Xiaoling Zeng, Shanghai (CN); Mohammad Abdul Kaium, Shanghai (CN); Yujie Zhou, Shanghai (CN)

(73) Assignees: Cellular Biomedicine Group (Shanghai) Ltd., Shanghai (CN); Cellular Biomedicine Group (Wuxi) Ltd., Wuxi, Jiangsu (CN)

( * ) Notice: Subject to any disclaimer, the term of this patent is extended or adjusted under 35 U.S.C. 154(b) by 0 days.

(21) Appl. No.: 15/947,231

(22) Filed: Apr. 6, 2018

(65) Prior Publication Data
US 2018/0296605 A1    Oct. 18, 2018

Related U.S. Application Data

(62) Division of application No. 14/765,755, filed as application No. PCT/CN2014/071716 on Jan. 28, 2014, now Pat. No. 9,956,250.

(30) Foreign Application Priority Data

Feb. 4, 2013   (CN) .......................... 2013 1 0044272

(51) Int. Cl.
| A61K 35/28 | (2015.01) |
| A61K 35/44 | (2015.01) |
| A61K 38/20 | (2006.01) |
| A61K 38/18 | (2006.01) |
| A61K 38/19 | (2006.01) |

(52) U.S. Cl.
CPC .............. *A61K 35/28* (2013.01); *A61K 35/44* (2013.01); *A61K 38/1833* (2013.01); *A61K 38/1841* (2013.01); *A61K 38/1858* (2013.01); *A61K 38/1866* (2013.01); *A61K 38/193* (2013.01); *A61K 38/2013* (2013.01); *A61K 38/2066* (2013.01)

(58) Field of Classification Search
CPC .... C12N 5/0667; C12N 5/0668; A61K 35/28; A61K 35/44; A61K 2300/00
See application file for complete search history.

(56) References Cited

U.S. PATENT DOCUMENTS

2012/0164113 A1    6/2012   Victor

FOREIGN PATENT DOCUMENTS

| CN | 101420964 | 4/2009 |
| WO | 2012/091911 | 5/2012 |

OTHER PUBLICATIONS

Gao, Songtao, "Experimental Study of Tissue-engineered peripheral nerve repairing sciatic nerve gap of rats", China Doctoral Dissertations Full-text Database, Jan. 31, 2008, (110 pages, including English abstracts on pp. V-VIII of reference copy; See also ISR).
International Search Report, dated May 8, 2014; PCT/CN2014/071716 (8 pages).
Blaber et al., Analysis of in vitro secretion profiles from adipose derived cell population, J. of Translational Medicine, 2012, 10:172.

*Primary Examiner* — Ruth A Davis
(74) *Attorney, Agent, or Firm* — Hamre, Schumann, Mueller & Larson, P.C.

(57) ABSTRACT

Provided are uses of allogeneic interstitial vessel-layer cells and allogeneic mesenchymal progenitor cells in the preparation of a pharmaceutical composition for preventing or treating osteoarthritis (OA). Also provided is a pharmaceutical composition containing the allogeneic interstitial vessel-layer cells and the allogeneic mesenchymal progenitor cells.

9 Claims, 5 Drawing Sheets

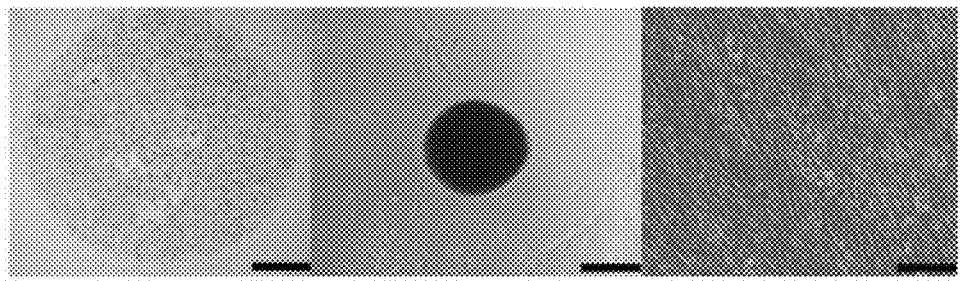
Fig 4.1　　　　Fig 4.2　　　　Fig 4.3
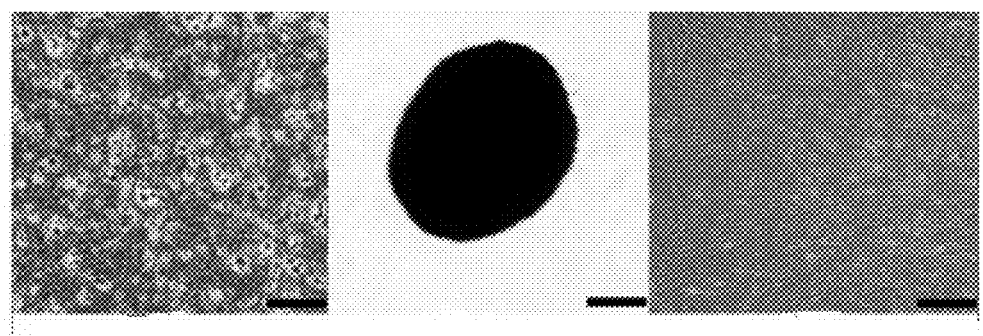
Fig 4.4　　　　Fig 4.5　　　　Fig 4.6
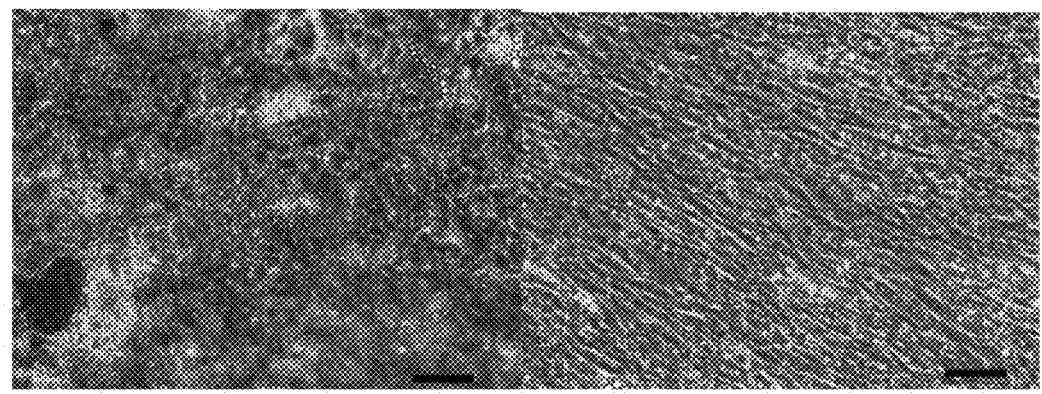
Fig 5.1　　　　　　　　Fig 5.2

USE OF ALLOGENEIC INTERSTITIAL VESSEL-LAYER CELL AND ALLOGENEIC MESENCHYMAL PROGENITOR CELL FOR PREVENTING OR TREATING OSTEOARTHRITIS

FIELD OF THE INVENTION

The present invention belongs to the field of stem cells and biomedicine. Specifically, the present invention relates to the use of allogeneic interstitial vessel-layer cells and allogeneic mesenchymal progenitor cells for preventing or treating osteoarthritis.

BACKGROUND OF THE INVENTION

Osteoarthritis (OA) is a chronic joint disease characterized by degeneration and destruction of articular cartilage as well as bone hyperplasia. The morbidity of OA is 50% in populations over 60 and 80% in those over 75, and the disability rate of OA is up to 53% ("*Osteoarthritis Treatment Guidelines* (Rev)", Chinese Medical Association of Orthopaedics, 2007). OA is common in joints suffering from heavy burden and frequent activities, such as knee, namely knee osteoarthritis (KOA). Knee osteoarthritis is one of major diseases which lead to activity dysfunction in elder people, and leads to heavy financial burden to health insurance and family.

At present, the general principle for treating knee osteoarthritis (KOA) is the combination of drug and non-drug therapy with surgeries when necessary so as to achieve the relief or elimination of pain, deformity correction, joint function improvement or restoration, thereby improving quality of life.

Drug therapy mainly comprises analgesics such as non-steroidal anti-inflammatory drugs (NSAIDs), intra-articular injection of hyaluronic acid (HA) or corticosteroids, drugs for improving the state of illness and cartilage protection agents, etc. These drugs can to some extent delay the course of the disease and improve patients symptoms. However, the efficacy is limited, the pathological progression is irreversible, the cartilage damage is irreparable, and most of the drugs have obvious side effects.

When conventional therapy turns out to be invalid, surgeries are needed for the patients with joint deformity and joint dysfunction. Surgical treatments are conducted mainly by arthroscopic (endoscope) and open surgery. Even though they can temporarily relieve pain, they are expensive and have poor long-term effect. It is reported those 10-15 years after joint replacement surgery, the prosthesis started to get worn or even loosen. Therefore, the present studies aim at exploring novel treatments and repair strategies.

Tissue engineering dedicates in autologous chondrocyte transplantation or matrix-induced autologous chondrocyte transplantation and provides the possibility of long-term solution for biologically repairing or regenerating the degraded joint tissues. However, this type of technology is mainly limited in treating large cartilage defects. Factors such as the damages to the donors' site, the dedifferentiation and the limited survival time of cartilage cells make the method being unsuitable for KOA patients.

Currently, many studies are targeting to allogeneic mesenchymal progenitor cells from other sources, such as adipose allogeneic mesenchymal progenitor cells. Adipose allogeneic mesenchymal progenitor cells are characterized by their extensive sources, safety, low immunogenicity and excellent immunoregulation ability, thereby exhibiting a unique effect on the treatments of KOA. The applicant has also developed autologous adipose mesenchymal progenitor cells with definite clinical curative effects. However, autologous adipose can not be provided by some KOA patients, such as patients having infectious diseases, or the old and emaciated ones, resulting in those patients unable to use autologous fat mesenchymal progenitor cells to treat KOA.

Therefore, the applicant develops allogeneic mesenchymal progenitor cells to meet the demands of those patients.

SUMMARY OF THE INVENTION

The object of the present invention is to provide the use of allogeneic interstitial vessel-layer cell and allogeneic mesenchymal progenitor cells for treatment or prevention of knee osteoarthritis.

The first aspect of the invention is providing a use of allogeneic interstitial vessel-layer cells (SVF) or allogeneic mesenchymal progenitor cells (haMPCs) for preparing pharmaceutical composition(s) for preventing and/or treating osteoarthritis.

In another preferred embodiment, said osteoarthritis is selected from the group consisting of knee osteoarthritis, spinal osteoarthritis, hip osteoarthritis, and the combination thereof.

In another preferred embodiment, said osteoarthritis is knee osteoarthritis.

In another preferred embodiment, said allogeneic interstitial vessel-layer cells are allogeneic interstitial vessel-layer cell populations.

In another preferred embodiment, said allogeneic mesenchymal progenitor cells are allogeneic mesenchymal progenitor cell populations.

In another preferred embodiment, said allogeneic interstitial vessel-layer cells have one or more features selected from the following group:

(i) more than 30% of the cells having surface antigen CD29;
(ii) more than 50% of the cells having surface antigen CD73;
(iii) more than 85% of the cells having surface antigen CD49d;
(iv) more than 55% of the cells having surface antigen CD90.

In another preferred embodiment, more than 35% of the cells have surface antigen CD29.

In another preferred embodiment, more than 55% of the cells have surface antigen CD73.

In another preferred embodiment, more than 90% of the cells have surface antigen CD49d.

In another preferred embodiment, more than 60% of the cells have surface antigen CD90.

In another preferred embodiment, said allogeneic interstitial vessel-layer cells have one or more features selected from the following group:

(v) less than 85% of the cells having surface antigen CD34;
(vi) less than 15% of the cells having surface antigen CD45.

In another preferred embodiment, less than 80% of the cells have surface antigen CD34.

In another preferred embodiment, less than 12% of the cells have surface antigen CD45.

In another preferred embodiment, said allogeneic interstitial vessel-layer cells secrete cytokines are selected from the group consisting of stem cell growth factor (HGF), vascular endothelial growth factor (VEGF), platelet-derived growth factor (PDGF), transforming growth factor β (TGF-β), granulocyte-macrophage colony-stimulating factor (GM-CSF), interleukin-2 (IL-2), interleukin-10 (IL-10), and the combinations thereof.

In another preferred embodiment, said allogeneic interstitial vessel-layer cells are allogeneic interstitial vessel-layer cell populations.

In another preferred embodiment, concentration of stem cell growth factor (HGF) secreted from allogeneic interstitial vessel-layer cells is ≥0.5 ng/ml, preferably ≥0.8 ng/ml.

In another preferred embodiment, concentration of vascular endothelial growth factor (VEGF) secreted from allogeneic interstitial vessel-layer cells is ≥35 pg/ml, preferably ≥40 pg/ml.

In another preferred embodiment, concentration of transforming growth factor β (TGF-β) secreted from allogeneic interstitial vessel-layer cells is ≥150 pg/ml, preferably ≥180 pg/ml.

In another preferred embodiment, concentration of interleukin-2 (IL-2) secreted from allogeneic interstitial vessel-layer cells is ≥15 pg/ml, preferably ≥20 pg/ml, more preferably ≥30 pg/ml.

In another preferred embodiment, concentration of interleukin-10 (IL-10) secreted from allogeneic interstitial vessel-layer cells is ≥15 pg/ml, preferably ≥20 pg/ml, more preferably ≥30 pg/ml, most preferably ≥40 pg/ml.

In another preferred embodiment, said allogeneic mesenchymal progenitor cells have one or more features selected from the following group:

(i) more than 95% of the cells having surface antigen CD90;
(ii) more than 95% of the cells having surface antigen CD73;
(iii) more than 95% of the cells having surface antigen CD29;
(iv) more than 95% of the cells having surface antigen CD49d.

In another preferred embodiment, more than 98% of the cells have surface antigen CD90.

In another preferred embodiment, more than 98% of the cells have surface antigen CD73.

In another preferred embodiment, more than 98% of the cells have surface antigen CD29.

In another preferred embodiment, more than 98% of the cells have surface antigen CD49d.

In another preferred embodiment, said allogeneic mesenchymal progenitor cells have one or more features selected from the following group:

(v) less than 2% of the cells having surface antigen HLA-DR;
(vi) less than 2% of the cells having surface antigen Actin;
(vii) less than 2% of the cells having surface antigen CD34;
(viii) less than 2% of the cells having surface antigen CD45;
(ix) less than 2% of the cells having surface antigen CD14.

In another preferred embodiment, less than 1% of the cells have surface antigen HLA-DR.

In another preferred embodiment, less than 1% of the cells have surface antigen Actin.

In another preferred embodiment, less than 1% of the cells have surface antigen CD34.

In another preferred embodiment, less than 1% of the cells have surface antigen CD45.

In another preferred embodiment, less than 1% of the cells have surface antigen CD14.

In another preferred embodiment, said allogeneic mesenchymal progenitor cells secrete cytokines selected from the group consisting of vascular endothelial growth factor (VEGF), transforming growth factor α (TGF-α), transforming growth factor β (TGF-β), granulocyte-macrophage colony-stimulating factor (GM-CSF), hepatocyte growth factor (HGF), platelet-derived factor (PDGF), interleukin-2 (IL-2), interleukin-4 (IL-4), and interleukin-10 (IL-10).

In another preferred embodiment, concentration of vascular endothelial growth factor (VEGF) secreted from the allogeneic mesenchymal progenitor cells is ≥10 pg/ml, preferably ≥15 pg/ml.

In another preferred embodiment, concentration of transforming growth factor β (TGF-β) secreted from the allogeneic mesenchymal progenitor cells is ≥300 pg/ml, preferably ≥400 pg/ml.

In another preferred embodiment, concentration of granulocyte-macrophage colony-stimulating factor (GM-CSF) secreted from the allogeneic mesenchymal progenitor cells is ≥30 ng/ml, preferably ≥40 ng/ml.

In another preferred embodiment, concentration of hepatocyte growth factor (HGF) secreted from the allogeneic mesenchymal progenitor cells is ≥0.4 ng/ml, preferably ≥0.5 ng/ml.

In another preferred embodiment, concentration of platelet-derived factor (PDGF) secreted from the allogeneic mesenchymal progenitor cells is ≥0.008 ng/ml, preferably ≥0.01 ng/ml.

In another preferred embodiment, concentration of interleukin-2 (IL-2) secreted from the allogeneic mesenchymal progenitor cells is ≥25 pg/ml, preferably ≥30 pg/ml.

In another preferred embodiment, concentration of interleukin-10 (IL-10) secreted from the allogeneic mesenchymal progenitor cells is ≥30 pg/ml, preferably ≥40 pg/ml.

The second aspect of the invention is providing a pharmaceutical composition for preventing and/or treating of osteoarthritis, said pharmaceutical composition comprises: allogeneic interstitial vessel-layer cells (SVF) and allogeneic mesenchymal progenitor cells (haMPCs) with effective dose(s), and pharmaceutically acceptable carriers.

In another preferred embodiment, said pharmaceutical composition is a subcutaneous injection agent.

In another preferred embodiment, said pharmaceutically acceptable carriers comprises (but not limited to): saline, buffer solution, dextrose, water, glycerol, ethanol, and combinations thereof.

In another preferred embodiment, concentration of said allogeneic interstitial vessel-layer cells is $0.1$-$100 \times 10^4$ cells/ml, preferably $1$-$10 \times 10^4$ cells/ml, more preferably $2 \times 10^5$ cells/ml.

In another preferred embodiment, concentration of said allogeneic mesenchymal progenitor cells is $0.1$-$100 \times 10^4$ cells/ml, preferably $1$-$10 \times 10^4$ cells/ml, more preferably $2 \times 10^5$ cells/ml.

The third aspect of the invention is providing a method for preventing and/or treating osteoarthritis comprising step of: administering allogeneic interstitial vessel-layer cells (SVF) or allogeneic mesenchymal progenitor cells (haMPCs), or administering a pharmaceutical composition comprising allogeneic interstitial vessel-layer cell (SVF) or allogeneic mesenchymal progenitor cells (haMPCs) to a subject in need.

In another preferred embodiment, said subject is human or non-human mammal, preferably human.

In another preferred embodiment, said method comprises steps of:

(1) administering allogeneic interstitial vessel-layer cells to a subject in need; and (2) administering allogeneic mesenchymal progenitor cells to a subject in need.

In another preferred embodiment, administration site is inside of arthrosis of said subject.

In another preferred embodiment, interval time between step (1) and step (2) is more than one month, and/or more than 3 month.

It should be understood that, in the present invention, each of the technical features specifically described above and below (such as those in the Examples) can be combined with each other, thereby constituting new or preferred technical solutions which need not be specified again herein.

DESCRIPTION OF FIGURES

The following figures are used to illustrate the specific embodiments of the present invention instead of limiting the scope of the present invention defined by the claims.

FIG. 3A shows the change of secretion amounts of VEGF from haMPCs after a 24 h stimulation by LPS; FIG. 3B shows the effect of hypoxia stimulation on the secretion amounts of VEGF from haMPCs.

FIG. 4.1-FIG. 4.6 show the result of haMPCs chondrogenic induction experiments.

FIG. 5.1 and FIG. 5.2 show the result of haMPCs osteogenic induction experiments.

DETAILED EMBODIMENTS

Figure 1:
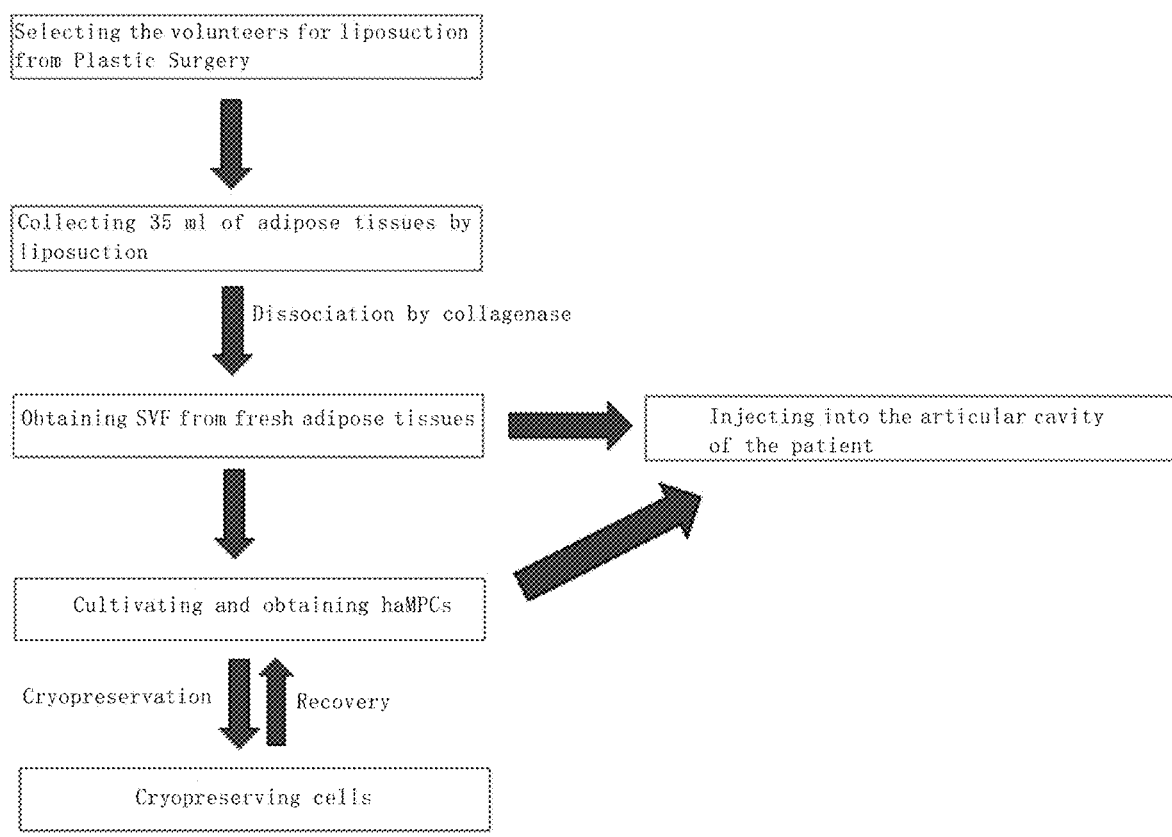
FIG. 1 shows the process of treating KOA by mixed treatment of allogeneic SVF and haMPCs.
Figure 2A:
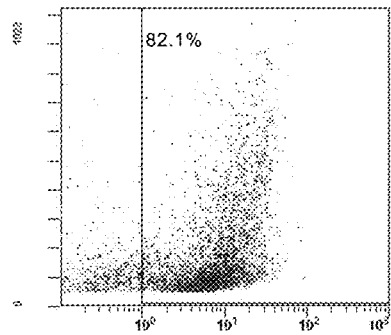
FIG. 2A-FIG. 2I show the surface antigen detection results of SVF, wherein FIG. 2A-FIG. 2I respectively shows the antigen detection result of CD34, CD29, CD73, CD49d, CD90, CD14, CD45, Actin and HLA-DR.
Figure 2B:
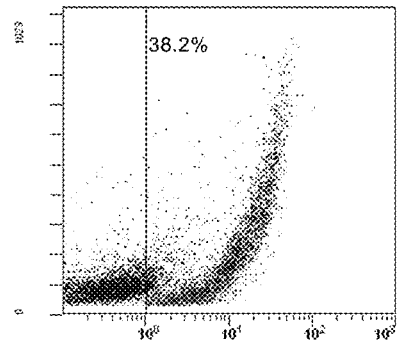
Figure 2C:
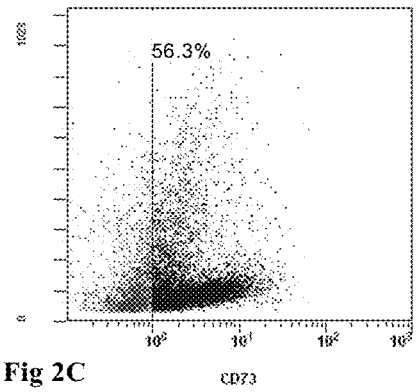
Figure 2D:
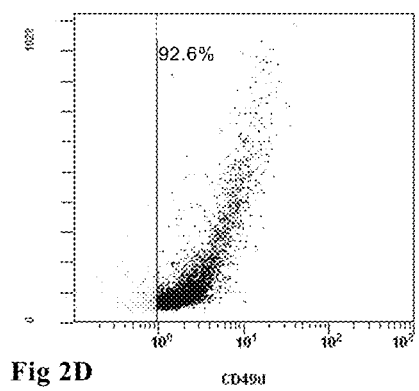
Figure 2E:
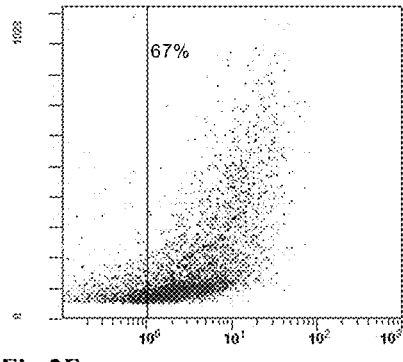
Figure 2F:
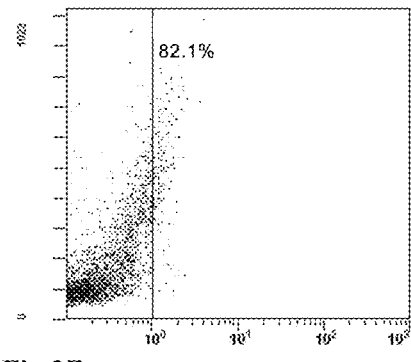
Figure 2G:
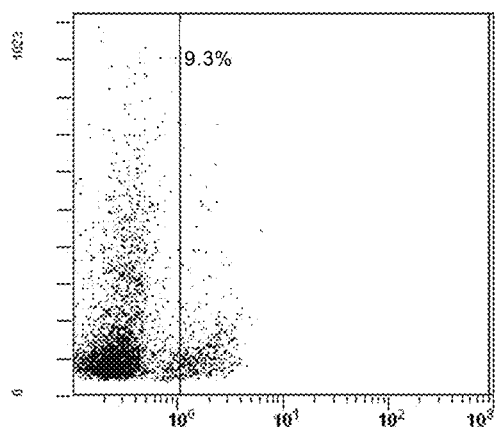
Figure 2H:
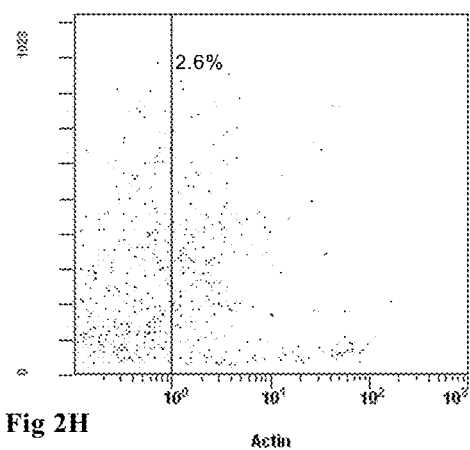
Figure 2I:
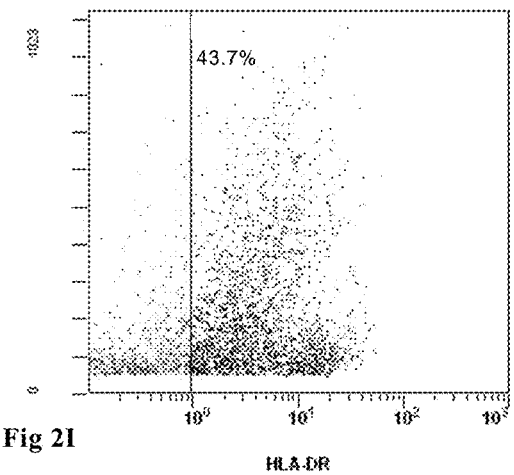

Upon extensive and intensive studies, the inventor has unexpectedly discovered for the first time that allogeneic interstitial vessel-layer cells and allogeneic mesenchymal progenitor cells possess an extremely excellent effect on preventing and/or treating osteoarthritis. Specifically, prominent effects on preventing or treating osteoarthritis can be achieved by administrating the allogeneic interstitial vessel-layer cells or allogeneic mesenchymal progenitor cells derived from allogeneic adipose according to the present invention, or pharmaceutical composition comprising the allogeneic interstitial vessel-layer cells or allogeneic mesenchymal progenitor cells derived from allogeneic adipose to a subject in need. Allogeneic mesenchymal progenitor cells possess excellent ability for cytokine secretion, and can repair the body injuries under suitable conditions in vivo. Allogeneic interstitial vessel-layer cells and allogeneic mesenchymal progenitor cells possess chondrogenic differentiation abilities and osteogenic differentiation abilities. The present invention also provides a method for preventing and/or treating osteoarthritis, and a pharmaceutical composition comprising allogeneic interstitial vessel-layer cells or allogeneic mesenchymal progenitor cells. The present invention is completed on this basis.

Terms

As used herein, terms "more than" and "less than" includes the number itself, e.g., "more than 95%" means≥95%, "less than 0.2%" means≤0.2%.

Osteoarthritis

As used herein, terms "osteoarthritis" and "OA" can be used interchangeably.

Osteoarthritis is a chronic joint disease with main changes of degeneration of articular cartilage surface and secondary hyperostosis manifesting joint pain and stiffness. X-ray shows joint space narrowing, subchondral bone eburnation, bone trabecula fracture, sclerosis, cystic degeneration, lip-like hyperplasia in joint edge, capitulum deformation in late stage, unevenness in articular surface, articular cartilage denudation, and intra-articular free bodies formed by fallen fracture bones.

In the present invention, said osteoarthritis can be any osteoarthritis selected from the following group consisting of knee osteoarthritis, spinal osteoarthritis, hip osteoarthritis, and the combinations thereof. The osteoarthritis of the present invention is preferably knee osteoarthritis.

Adipose

Fat is a good source for plastics and anti-aging treatments. Adipose tissue materials can be derived from the parts of waist, hips, abdomen, thighs, upper arms, etc. Those skilled in the art may obtain adipose tissues by common techniques and methods including (but not limited to) suction or surgical separation, etc.

In the present invention, adipose tissues or adipose sources are not specifically limited. They may be derived from any part of animal or human adipose tissues, preferably human adipose tissues. Preferably, the adipose tissues may be tissues from the parts of waist, hips, abdomen, thighs, upper arms, etc.

Allogeneic Interstitial Vessel-Layer Cells

As used herein, term "allogeneic interstitial vessel-layer cell", "SVF", or "stromal vascular fragment(s)" can be used interchangeably.

Allogeneic interstitial vessel-layer cells are a type of stem cells with multi-directional differentiation potency separated from adipose tissues. SVF can proliferate stably in vitro with low attenuation rate. They can be easily obtained from a large reservation amount in the body, they are suitable for large-scale cultivation and do little harm to the body, and they can be obtained from extensive sources with low antigenicity, thereby suitable for allograft. SVF is the most important component in stem cell-assisted fat tranplant. Cell clusters formed by mixture containing varieties of cells isolated from adipose tissues by collagenase digestion are called stromal vascular fragments. Stromal vascular fragments comprise abundant mesenchymal cells, which can differentiate into multiple lineages of cells, thus being the ideal seed cells in regenerative medicine, tissue engineering, etc.

As used herein, the terms "separation method" and "SVF separation method" can be used interchangeably, both referring to the method or the processes for obtaining isolated SVF from the original adipose tissues. The obtained SVF adipocyte materials are firstly washed to remove blood cells; then subjected to fat breaking and digestion. Undigested tissues are removed to obtain a filtrate containing SVF and SVF are obtained by centrifugation. Obtained SVF may be used for further passage, cultivation or cryopreservation.

In a preferred embodiment, the separation of SVF may include (but not limited to) the following steps: washing the adipose obtained from liposuction by PBS twice, and then digesting in 37° C. condition for 30 mins by collagenase, obtaining SVF fragments of high density mainly comprising mesenchymal cells, endothelial cells and parietal cells upon centrifugation at 1200 g for 10 mins. Besides, SVF further comprises some vascular derived cells, such as leukocytes and erythrocytes, etc. The various cells have synergistic effects.

Antigen Detection of Allogeneic Interstitial Vessel-Layer Cells

SVFs used in the present invention are highly purified and substantially free of other types of cells or stem cells. This can be verified by detection of cell surface antigens.

SVF has a variety of specific antigens and receptors, mainly CD3, CD13, D29, CD34, CD45, CD49e, CD59, CD73, CD90, CD105, or HLA-ABC, etc.

CD34 antigen is a highly glycosylated type I transmembrane protein, which is s electively expressed on the surface of human hematopoietic stem cells (HSC), progenitor cells (PC) and endothelial cells (EC). The percentage of adipose tissue progenitor cells with CD34 in the total stem cells is preferably ≤0.2%, more preferably ≤0.2%.

CD45 exists on the surface of all blood cells, including hematopoietic stem cells and osteoclasts. The percentage of adipose tissue stem cells with CD45 in the total progenitor cells is preferably ≤0.1%.

CD29, CD73, CD49d, CD90 etc. mainly exist on the surface of adipose allogeneic mesenchymal progenitor cells.

The percentage of SVF with CD29 in the total stem cells is preferably ≥30%, more preferably ≥32%, most preferably ≥35%.

The percentage of SVF with CD73 in the total stem cells is preferably ≥50%, more preferably ≥60%, most preferably ≥70%.

The percentage of SVF with CD49d in the total stem cells is preferably ≥85%, more preferably ≥90%, most preferably ≥95%.

The percentage of SVF with CD90 in the total stem cells is preferably ≥55%, more preferably ≥60%, most preferably ≥65%.

One skilled in the art can detect the purity and differentiation degree of SVF by common methods, such as flow cytometry. During detection, different targeted specific antibodies are added. The antibodies can be intact monoclonal or polyclonal antibodies, or antibody fragments having immunological activity, such as Fab' or (Fab) 2 fragments; antibody heavy chains; antibody light chains; single-chain Fv molecule obtained by genetic engineering (Ladner et al., U.S. Pat. No. 4,946,778); or chimeric antibodies, such as antibodies having murine antibody binding specificity while still keeping the antibody portions from the human antibody. After the added antibodies binding with the cell surface antigens for a certain time, the cells are automatically analyzed and sorted by flow cytometry.

Mesenchymal Progenitor Cells Derived from Allogeneic Adipose

As used herein, the term "mesenchymal progenitor cells derived from allogeneic adipose", "haMPCs" or "adipose tissue-derived mesenchymal progenitor cells" has the same meaning and can be used interchangeably.

The mesenchymal progenitor cells derived from allogeneic adipose are preferably allogeneic mesenchymal progenitor cells derived from human allogeneic adipose.

Those skilled in the art can separate and cultivate haMPCs by conventional methods. In a preferred embodiment, the following steps are comprised:

a. dispensing adipose: transferring extracted adipose into centrifuge tube, wherein, the extracted adipose is divided into two parts with one part for washing and digestion by collagenase to prepare SVF cell suspension for direct autotransfusion, and the other part for further culture after obtaining SVF to give adipose progenitor cells;

b. digesting adipose: adding enzymes into centrifuge tube, subjecting to adipose digestion in constant temperature vibrator. Upon digestion, discarding digested adipose in upper layer; and collecting precipitate for washing;

c. filtrating: adding cell washing liquor and mixing to homogenous; subjecting the cells to cell counting upon filtration by filter screen, centrifugation and washing for precipitation. The filtered cells are stromal vascular fraction cells SVF. SVF is a mixture of a variety of cells isolated from adipose tissue and it is a cell population formed by various allogenic cells, wherein, MPCs-like cells, endothelial (progenitor) cells, vascular smooth muscle cells and other parts of blood-derived cells including granulocytes, monocytes, lymphocytes and the like are included;

d. preparing for SVF suspension: preparing the filtered SVF cells into 5 ml cell suspension; injecting the suspension into 100 ml saline bag upon a syringe suction;

e. culturing cells: inoculating the cells into a culture flask, wherein, the inoculation density is adjusted according to the cell counts, and subjecting the product to a $CO_2$ incubator for culture;

f. passaging: culturing the adherent cells for 5-7 days to form colonies after a few adherent allogeneic mesenchymal progenitor cells start to appear upon about a 3-day inoculation. Digesting, passaging, and then collecting the cells for cell counting. Subjecting the primary adherent cells to passage at a ratio of 1:1-2 and culture for 2-3 weeks. Collecting the cells (allogeneic adipose derived progenitor cells);

g. preparing suspension of progenitor cells derived from the adipose: centrifuging and washing the collected progenitor cells derived from adipose, and then injecting saline to produce a cell suspension.

Antigen Detection of Allogeneic Mesenchymal Progenitor Cells Derived from Allogeneic Adipose The mesenchymal progenitor cells derived from allogeneic adipose used in the present invention are highly purified and have excellent activity.

Those skilled in the art can detect the surface antigen of allogeneic mesenchymal progenitor cells by conventional methods, for example, by flow cytometry.

The allogeneic mesenchymal progenitor cells derived from allogeneic adipose have various specific antigens, and receptors, mainly comprising: CD29, CD73, CD90, CD49d, etc.

The percentage of allogeneic mesenchymal progenitor cells with CD73 antigen in the total allogeneic mesenchymal progenitor cells is ≥95%, preferably ≥98%, more preferably ≥99%, most preferably is 100%.

The percentage of allogeneic mesenchymal progenitor cells with CD90 antigen in the total allogeneic mesenchymal progenitor cells is ≥95%, preferably ≥98%, more preferably ≥99%, most preferably is 100%.

The percentage of allogeneic mesenchymal progenitor cells with CD29 antigen in the total allogeneic mesenchymal progenitor cells is ≥95%, preferably ≥98%, more preferably ≥99%, most preferably is 100%.

The percentage of allogeneic mesenchymal progenitor cells with CD49d antigen in the total allogeneic mesenchymal progenitor cells is ≥95%, preferably ≥98%, more preferably ≥99%, most preferably is 100%.

The negative markers of the allogeneic mesenchymal progenitor cells derived from allogeneic adipose comprise: HLA-DR, Actin, CD34, CD45, CD14, etc.

The percentage of allogeneic mesenchymal progenitor cells with HLA-DR antigen in the total allogeneic mesenchymal progenitor cells is ≤2%, preferably ≤1%, more preferably ≤0.5%, most preferably no HLA-DR antigen.

The percentage of allogeneic mesenchymal progenitor cells with Actin antigen in the total allogeneic mesenchymal progenitor cells is ≤2%, preferably ≤1%, more preferably ≤0.5%, most preferably no Actin antigen.

The percentage of allogeneic mesenchymal progenitor cells with CD34 in the total allogeneic mesenchymal progenitor cells is ≤2%, preferably ≤1%, more preferably ≤0.5%, most preferably no CD34.

The percentage of allogeneic mesenchymal progenitor cells with CD45 in the total allogeneic mesenchymal progenitor cells is ≤2%, preferably ≤1%, more preferably ≤0.5%, most preferably no CD45.

The percentage of allogeneic mesenchymal progenitor cells with CD14 in the total allogeneic mesenchymal progenitor cells is ≤2%, preferably ≤1%, more preferably ≤0.5%, most preferably no CD14.

The haMPCs used in the present invention are preferably human derived haMPCs which can secrete a large amount of cytokines such as VEGF, TGF-α, TGF-β, GM-CSF, HGF, PDGF, IL-2, IL-4, IL-10, while having remarkable clonogenic capacity and low immunogenicity.

Those skilled in the art can use, treat, administer or do other operations to the haMPCs by conventional methods. For example, each batch of haMPCs should pass the sterile, endotoxin and mycoplasma tests and the DNA establishing identification before it is released or used. Each batch of issued cells should meet the requirements of: cell viability ≥95%, cell purity (positive markers ≥95%, negative markers <2%), and negative in haMPCs acute toxicity and allergy test results. Each of the above should have a corresponding test report.

Pharmaceutical Compositions and the Use Thereof

The present invention also provides a pharmaceutical composition, which comprises allogeneic interstitial vessel-layer cells or allogeneic mesenchymal progenitor cells with effective amounts, and pharmaceutically acceptable carriers.

Usually, allogeneic interstitial vessel-layer cells and allogeneic mesenchymal progenitor cells can be prepared in nontoxic, inert and pharmaceutically acceptable aqueous carrier medium, such as saline, of which the pH is usually about 5-8, preferably, about 7-8.

As used herein, the term "effective amount" or "effective dose" refers to the amount that can produce function or activity on humans and/or animals and can be accepted by human and/or animal.

As used herein, "pharmaceutically acceptable" component is a substance which can be applied to humans and/or mammals without undue adverse side effects (such as toxicity, irritation and allergic reactions), that is to say, substances of reasonable benefit/risk ratio. The term "pharmaceutically acceptable carrier" refers to a carrier for administration of a therapeutic agent, including various excipients and diluents.

The carriers of the pharmaceutical compositions of the present invention include (but are not limited to): saline, buffer solution, glucose, water, glycerol, ethanol, and combinations thereof. Pharmaceutical preparations usually should match the method of administration. The pharmaceutical compositions of the invention may be prepared in the form of injections, for example, prepared with saline or aqueous solutions containing glucose and other adjuvants by conventional methods. The pharmaceutical compositions preferably manufactured under sterile conditions. The amount of active ingredient administered is a therapeutically effective amount. Pharmaceutical formulations of the present invention may also be prepared into sustained release formulations.

The allogeneic interstitial vessel-layer cells and the effective amount of allogeneic mesenchymal progenitor cells of the present invention may vary with the mode of administration and the severity of the diseases being treated. A preferred option of the effective amount may be based on a variety of factors determined by those skilled in the art (e.g., via clinical trials). The factors include, but are not limited to: the pharmacokinetic parameters such as bioavailability, metabolism, half-life and the like; the severity of the patient's disease to be treated, body weight or immune status of a patient, the route of administration, etc.

The pharmaceutical compositions of the present invention are preferably subcutaneous injection reagents. In another preferred embodiment, the concentration of the allogeneic interstitial vessel-layer cells of subcutaneous injection reagent is $0.1$-$100 \times 10^4$ cells/ml, preferably $1$-$10 \times 10^4$ cells/ml, more preferably $2 \times 10^5$ cells/ml; and/or the concentration of the allogeneic mesenchymal progenitor cells is $0.1$-$100 \times 10^4$ cells/ml, preferably $1$-$10 \times 10^4$ cells/ml, more preferably $2 \times 10^5$ cells/ml.

The present invention also provides a method of using the pharmaceutical compositions of the present invention, in a particular embodiment, comprising the following steps:

(1) administering allogeneic interstitial vessel-layer cells to a subject in need, a preferred administration site is the inside of arthrosis of the said subject; and (2) administering allogeneic mesenchymal progenitor cells to a subject in need, the preferred administration site is the inside of arthrosis of the said subject; the preferred administration time is one month after step (1), and/or two months.

Application process according to the invention is shown in FIG. 1.

The Main Merits of the Present Invention Comprise:

(1) The SVF and haMPCs of the present invention can be obtained form extensive sources;

(2) The SVF and haMPCs of the present invention is safe when they are used in vivo;

(3) The SVF and haMPCs of the present invention do not have any interspecies immune rejection when used in rats;

(4) After stimulated by LPS or hypoxia, etc, the expression levels of various cytokines of the haMPCs of the present invention significantly increased, haMPCs have relatively high cytokines secretion ability, and they can perform injury repairments under appropriate conditions in vivo;

(5) The haMPCs of the present invention have typical mesenchymal stem cell characteristics, which possess potential differentiative capacity under appropriate conditions in vivo, thus meeting the relative demand of the body;

(6) By the combination therapy of SVF and haMPCs of the present invention, the haMPCs can be transformed into cartilage cells and bone cells under certain induction conditions, thus, it can be used in the prevention or the treatment of osteoarthritis.

The present invention will be further illustrated below with reference to the specific examples. It should be understood that these examples are only to illustrate the invention but not to limit the scope of the invention. The experimental methods with no specific conditions described in the following examples are generally performed under the conventional conditions, such as conditions illustrated in Sambrook et al, Molecular Cloning: A Laboratory Manual (New York:

Cold Spring Harbor Laboratory Press, 1989), or according to the manufacture's instructions.

Example 1

Treating Knee Osteoarthritis (KOA) with SVF and haMPCs

Male patient, 53 years old, bilateral knee pain for over six years, exacerbated for one month. Continuous pain, only indoor walking can be tolerated, difficulty in climbing stairs, painful when walking on flat ground, accompanied by morning stiffness. X-ray examination showed: joint edge hyperplasia, osteophyte formation, joint space narrowing, and there being with sclerotic changes. WOMAC score 103. Diagnosis: moderate knee osteoarthritis.

About 30 ml of clean adipose extracted by Lipokit was obtained from the plastics (the fat provider was a 29-year-old healthy female seeking for liposuction from plastic surgery for weight loss. BMI before liposuction was 26.73). Stromal vascular fraction was separated from 10 ml newly obtained adipose tissues, digested by collagenase, filtrated, centrifugated to remove mature adipocytes to obtain SVF, and the SVF surface antigens were identified. The identification results were shown in FIG. 2A-FIG. 2I.

$1*10^7$ cells/2 ml of SVFs for each were intra-articularly injected to both sides of the patient. The remaining adipose tissues were separated and purified to culture for P2-P5 generations so as to get haMPCs. haMPCs were cryopreserved for further cultivation after recovery. The patient was subjected to another intra-articular injection bilaterally at the first month and the third month after the first injection. The amounts of the injection for each side was $1*10^7$/month/2 ml. Routine blood and urine tests, tests for indicators of hepatic and renal function, coagulation function, electrolytes, etc. were conducted at 24 hours, 72 hours, one week after each injection.

Results: No significant abnormalities was shown in the above examinations. Patient's pain was relieved, the mobility was significantly improved, and the pain during walking on flat ground and climbing stairs was relieved. X-ray examination showed that the articular surface was slightly improved comparing with the previous. WOMAC score was 62.

Example 2

The Identification of SVF and haMPCs
1. Flow Test

The cells were collected into a centrifuge tube upon the enzymatic digestion, of which the density of the cell suspension was adjusted to $1\times10^5$/mL and centrifuged for 5 min at 800 r/min (120 g). The supernatant was discarded. The resuspended cells were washed with 4° C. cold D-Hanks, the cell suspension was further centrifuged at 800 r/min for 5 min, and then the supernatant was discarded. The cells were resuspended to 1 mL with D-Hanks. 5~10 μL of the antibodies were added, the product was placed on ice for 30 mins and kept from light. The product was washed with D-Hanks, centrifuged, and the supernatant was discarded. The washing procedure was repeated for two or three times to ensure that the unbounded antibodies were completely removed. Finally, about 200 to 300 μL of D-Hanks was added to produce suspension, which was detected by flow cytometry (FIG. 2A-FIG. 2I).

The flow cytometry result of SVF is shown in Table 1.

TABLE 1

|  | CD29 | CD73 | CD49d | CD90 | CD14 | CD45 | CD34 | Actin | HLA-DR |
|---|---|---|---|---|---|---|---|---|---|
| SVF | 38.2% | 56.3% | 92.6% | 67% | 4.4% | 9.3% | 82.1% | 2.6% | 43.7% |

Analysis of the expression of cell surface antigen markers of SVF was performed by flow cytometry, the results showed: the percentage of SVF in the freshly isolated progenitor cells was 60%, and the content of hematopoietic progenitor cells was 70%, wherein, there are more mixed cells.

The flow test results of haMPCs are shown in Table 2.

TABLE 2

| Antibody | Percentage (%) | Antibody | Percentage (%) |
|---|---|---|---|
| CD90 | 99.91 | Actin | ~0% negative |
| CD29 | 99.96 | DR | ~0% negative |
| CD73 | 99.98 | CD34 | ~0% negative |
| CD49d | 99.92 | CD14 | ~0% negative |
|  |  | CD45 | ~0% negative |
|  |  | CD80 | 0.02 |
|  |  | CD86 | 0.01 |

2. The Detection of Cytokines Secreted from Cells

SVF and haMPCs were cultivated in the culture chamber for 48 h, the supernatant was taken for detecting the cytokines secreted by cells. The umbilical cord derived stem cells were used as the control group. The results are shown in Table 3.

TABLE 3

| Cytokines (unit) | hADMPCs | SVF | Umbilical cord derived stem cells |
|---|---|---|---|
| VEGF(pg/ml) | 19.81 | 24.13 | 18.21 |
| TGF-ß (pg/ml) | 398.00 | 180.11 | 415.02 |
| GM-CSF (ng/ml) | 43.66 | 62.50 | 63.46 |
| HGF (ng/ml) | 0.56 | 0.65 | 0.54 |
| PDGF (ng/ml) | 0.01 | 0.01 | 0.01 |
| IL-2(pg/ml) | 38.90 | 38.56 | 33.18 |
| IL-10(pg/ml) | 44.32 | 42.31 | 40.56 |

The results showed that: SVF and haMPCs have good cytokine secretion function, which is comparable to umbilical cord stem cells.

Example 3 haMPCs Stimulation Test (1) fresh and frozen haMPCs were separately placed in complete culture medium and 5% FBS medium for cultivation and VEGF secreted by haMPCs was detected.

Figure 3A:
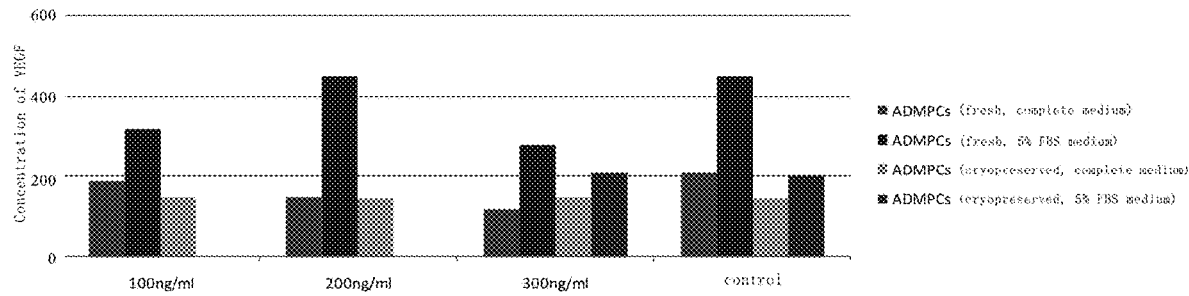
FIG. 3A and FIG. 3B show the change of secretion amounts of VEGF from haMPCs.

The results shows (FIG. 3A) that, the concentration of VEGF of fresh haMPCs in complete culture medium group decreased with the increase of LPS concentration; the concentration of VEGF of the fresh haMPCs in 5% FBS culture medium group was the same as that of the control group at 200 ng/ml, while the concentration of VEGF decreased at 100 ng/ml and 300 ng/ml respectively. The concentration of VEGF of the frozen haMPCs cultivated in complete culture medium substantially changed little when the concentrations of LPS increased. Generally, the concentration of VEGF cultivated in serum-containing culture medium was higher than that in the complete culture medium.

Figure 3B:
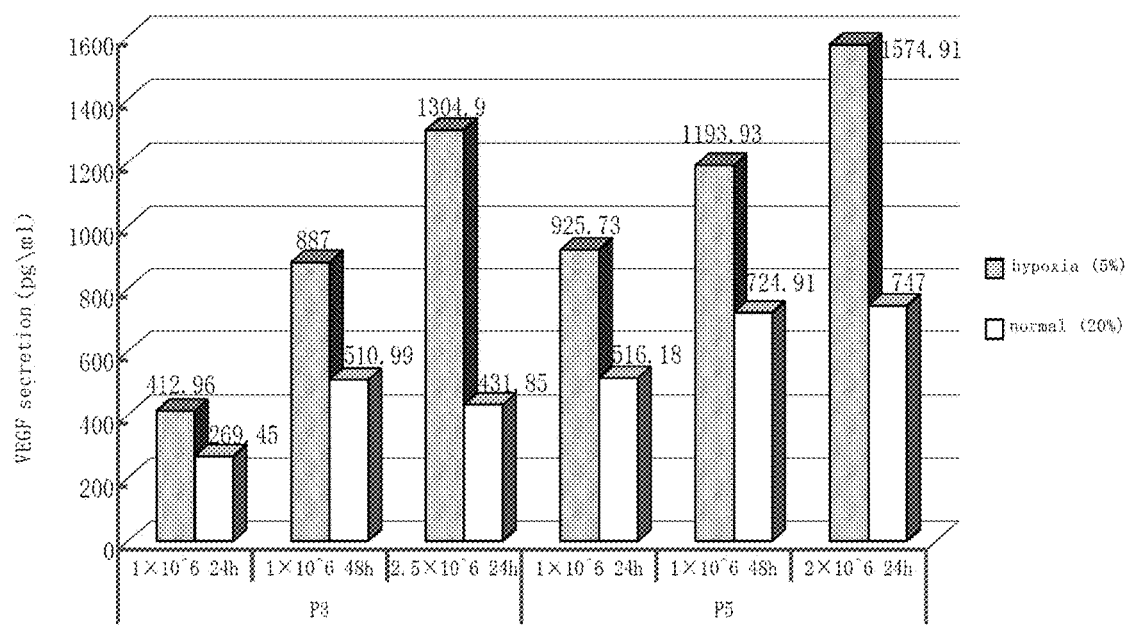

(2) the amounts of VEGF secreted from haMPCs under hypoxia stimulation were detected. It was found that VEGF secretion under hypoxia stimulation was 2-3 times of that of normal cultivation, and the secretion amount a of 48 hours was 2 times of that of 24 hours, the increment of VEGF was proportional to the increment of the concentration of cells (FIG. 3B).

Example 4

Chondrogenic Differentiation Test of haMPCs

A chondrogenic differentiation kit GIBCO STEMPRO was employed to prepare chondrogenic differential medium. haMPCs are digested and centrifuged to obtain P3 generation cells, and standard medium was used to prepare a cell suspension of $1.6 \times 10^{\wedge}7$ living cells/mL for later application. 5 μL cell suspension (the cell volume was $8 \times 10^4$) was drawn with a pipette, and seeded in the centers of the multi-well plate, and subjected to pre-incubation in a $CO_2$ incubator for 2 hours.

After the pre-incubation was over, 1 mL of chondrogenic differential complete medium preheated by 37° C. water bath was added into the test wells, and 1 mL of standard medium preheated by 1 mL 37° C. water bath was added into the control wells. The multi-well plate was placed into $CO_2$ incubator for culture under 37° C., 5% $CO_2$. During the culture, the medium in the corresponding plate wells were changed every 2-3 days. After a sufficient incubation time (7 or 14 days), 4% formalin solution (1 mL 40% formaldehyde dissolved in 9 mL of water) and 1% Alcian Blue dye (0.1 g Alcian Blue dissolved in 10 mL of 0.1N HCL) were prepared on the very day. Fixing and dyeing treatment was conducted to each well. The medium was removed by suction, and washed with DPBS for once. The cells were fixed with 4% formalin solution for 30 minutes. After fixation, DPBS was used for washing, and then 1% Alcian Blue solution (dissolved in 0.1N HCl) was added for staining for 30 minutes. 0.1N HCl was used for washing for three times, and distilled water was added to neutralize the acid. The experimental groups and the control groups were observed in the light microscope, and the pictures were saved. The experimental groups which successfully differentiated into cartilage cells turned blue after Alcian Blue staining due to the proteoglycan synthesized by chondrocyte.

Experiment results: On the seventh day of the experiment, the growth of the cells was observed, and wells A1, A3, and C1 were selected for image analysis. Upon observation, it can be seen that the cells concentrated in the center of inoculation region in well A1 (FIG. 4.1), while the cell shape was circular, which was approximate to cartilage cells, and the tightness of adherent of cells was ordinary, but could maintain its adherent state after medium was changed for several times; the cells in well A3 (FIG. 4.2) formed a highly aggregated globular cell mass structure, and a milk white spherical structure can be seen by naked eye; said structure was maintained after changing medium for several times, while the possibility of contamination was excluded; well C1 (FIG. 4.3) was added with standard medium as a control group, in which the cell morphology meets the standard of haMPCs adherent cells. Therefore, morphologically, there are significant differences between the haMPCs cultivated through differential medium and the control group.

The Alcian Blue staining results on the 14th day of the experiment indicated that, well C1 (4.6) did not show significant blue staining, while well A1 (FIG. 4.4) showed significant blue staining, which proved the existence of glycosaminoglycan synthesized by chondrocytes; and the staining of well A3 (FIG. 4.5) turned black-blue probably due to the over density of the cells. Therefore, the haMPCs cultivated in differentiation medium culture showed the differentiation characteristics of cartilage cell in classical chemical staining process.

In summary, the present example shows that the haMPCs of the present invention shows cartilage cell characteristics in cell morphology and classical chemical staining process when cultivated in differentiation medium culture, which indicates that haMPCs have the differentiation potential to chondrocytes.

Example 5 haMPCs Osteogenic Differentiation Test

An osteogenesis differentiation kit GIBCO STEMPRO was employed to prepare osteogenesis differential medium. haMPCs are digested and centrifuged to obtain P3 generation cells, and growth medium was used to prepare a cell suspension for later application. The haMPCs were seeded in a multi-well plate at a density of $5*10^3$ cells/$cm^2$, and subjected to pre-culture in a $CO_2$ incubator for 2 hours.

After the pre-incubation was over, 1 mL of chondrogenic differential complete medium preheated by 37° C. water bath was added into the test wells, and 1 mL of standard medium preheated by 1 mL 37° C. water bath was added into the control wells. The multi-well plate was placed into $CO_2$ incubator for culture under 37° C., 5% $CO_2$. During the culture, the medium in the corresponding plate wells were changed every 3-4 days. After a sufficient incubation time (>21 days), 4% formalin solution (1 mL 40% formaldehyde dissolved in 9 mL of water) and 1% Alcian Blue dye (0.1 g Alcian Blue dissolved in 10 mL of 0.1N HCL) were prepared on the very day. Fixing and dyeing treatment was conducted to each well. The medium was removed by suction, and washed with DPBS for once. The cells were fixed with 4% formalin solution for 30 minutes. After fixation, distilled water was used for washing, and then 2% Alcian Blue solution (pH 4.2) was added for staining for 2-3 minutes. distilled water was used for washing for three times. The experimental groups and the control groups were observed in the light microscope, and the pictures were saved.

Experimental results: On the 25th day of the experiment, the growth of cells was observed. The staining of experimental group showed that the nodular depositions were light brown, which was verified to be calcium depositions (FIG. 5.1); while the staining of the control group shown negative (FIG. 5.2).

In summary, the present example shows that haMPCs of the present invention shows osteocytes' characteristics in cell morphology and classical chemical staining process when cultivated in osteogenesis differentiation medium culture, which indicates that haMPCs have the differentiation potential to osteocytes.

Example 6

Animal Safety Test of SVF

Human adipose-derived stromal vascular cells (hSVF) was injected to SD rats through caudal vein. The cell doses were $1.0 \times 10^9/65$ kg for higher dose group and $5.0 \times 10^7/65$ kg for appropriate amount group. After 48 hours, no abnormal allergic reaction such as rash, piloelection, tachypnea, or tremors was observed. None of the rats died. The observation lasted for 10 weeks, and the rats were in good living conditions with normal body temperature, appetite and weight change. Wherein, the weight change in appropriate amount group, high-dose group and the control group, respectively, were raised to 502 g, 489 g and 493 g from the original 100 g. No significant difference was shown. Two weeks after the end of hSVF injection, the serum albumin, globulin and albumin/globulin levels in SD rats are all in the normal range (Table 4), and the indicators such as ALT, urea nitrogen, creatinine, glucose are all within normal range (Table 5). There was no significant difference between experimental group and control group. This study showed that intravenous injection of SVF are safe for rats, and the interspecies use of SVF did not cause immune rejection.

TABLE 4

| Groups | Albumin (g/L) | Globulin (g/L) | A/G |
|---|---|---|---|
| Control Group | 34.1 ± 1.80 | 36.2 ± 2.19 | 0.96 ± 0.07 |
| Appropriate Amount Group | 34.7 ± 0.61 | 32.5 ± 1.29 | 1.07 ± 0.05 |
| High Dose Group | 33.4 ± 0.51 | 34.3 ± 1.71 | 0.97 ± 0.09 |

TABLE 5

| Groups | ALT (U/L) | BUN (mmol/L) | Creatinine (umol/L) | Glucose (mmol/L) |
|---|---|---|---|---|
| Control Group | 62.1 ± 7.45 | 8.13 ± 1.70 | 36.7 ± 4.34 | 5.93 ± 1.12 |
| Appropriate Amount Group | 68.0 ± 7.30 | 6.88 ± 0.56 | 37.5 ± 2.08 | 6.38 ± 0.82 |
| High Dose Group | 64.9 ± 6.05 | 6.05 ± 0.50 | 36.7 ± 4.34 | 6.54 ± 0.37 |

Example 7

HaMPCs Safety Test after Cryopreservation and Recovery

The third generation (P3 generation) haMPCs obtained by passage and culture were cryopreserved, recovered and intravenously injected to the mice through caudal vein. The doses were $3.1 \times 10^2/g$ for the appropriate amount group and $1.5 \times 10^3/g$ for the high dose group. Continuous observation of 14 days was conducted after injection, the experimental animals were in good living condition, and no abnormal reaction was observed with body temperature, appetite and weight change. Wherein, weight gaining in the appropriate amount group and high dose group and control group was 11.8%, 13.9% and 14.3% respectively, and there was no significant difference between the groups. In vivo injection of haMPCs did not lead to significant effects on the liver, spleen, kidney, lung, brain, heart, thymus, thyroid or testis/ovary or other major organs, and the organ indexes did not change significantly. It was observed that liver, kidney, spleen and testis/ovary were structurally normal under light microscopy, and no pathological change such as mesenchyme hyperplasia, fatty infiltration or inflammatory cell infiltration was observed. Only in spleen from the experimental group, significant increase of megakaryocytes or polynuclear giant cells can be seen, which was probably related to the macrophages immune response caused by the injection of haMPCs and pending for further study. In this experiment, the mice blood biochemical parameters were within the normal range, and there were no significant differences among the appropriate amount group, the high dose group or the control group (Table 6-8). This study showed that intravenous injection of haMPCs was safe for mice, and the interspecies use of haMPCs did not cause immune rejection.

TABLE 6

| Groups | WBC ($*10^9$/L) | RBC ($*10^{12}$/L) | HB (g/L) | Pla ($*10^{12}$/L) |
|---|---|---|---|---|
| Control Group | 5.93 ± 1.35 | 8.69 ± 6.17 | 142.8 ± 6.17 | 494.0 ± 42.24 |
| Appropriate Amount Group | 7.50 ± 1.66 | 8.69 ± 0.44 | 145.8 ± 3.37 | 448.2 ± 49.8 |
| High Dose Group | 5.82 ± 1.80 | 8.90 ± 0.64 | 144.7 ± 8.69 | 477.5 ± 62.9 |

TABLE 7

| Groups | Albumin (g/L) | Globulin (g/L) | A/G |
|---|---|---|---|
| Control Group | 16.95.1 ± 0.85 | 36.83 ± 2.40 | 0.48 ± 0.04 |
| Appropriate Amount Group | 16.62 ± 0.98 | 36.80 ± 1.10 | 0.48 ± 0.04 |
| High Dose Group | 16.75.4 ± 0.76 | 37.67 ± 2.50 | 0.43 ± 0.05 |

TABLE 8

| Groups | GPT (U/L) | BUN (mmol/L) | Creatinine (umol/L) | Glucose (mmol/L) |
|---|---|---|---|---|
| Control Group | 23.0 ± 2.10 | 8.65 ± 0.23 | 5.83 ± 1.32 | 5.28 ± 0.39 |
| Appropriate Amount Group | 22.8 ± 2.86 | 7.46 ± 1.03 | 3.8 ± 1.10 | 6.3 ± 0.76 |
| High Dose Group | 22.67 ± 3.14 | 7.48 ± 3.98 | 5.83 ± 1.47 | 5.94 ± 0.64 |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:
1. A method for preventing and/or treating osteoarthritis, comprising: administering allogeneic interstitial vessel-layer cells (SVF) and allogeneic mesenchymal progenitor cells (haMPCs) to a subject in need thereof,
   wherein said allogeneic mesenchymal progenitor cells have one or more features selected from the group consisting of
   more than 95% of the allogeneic mesenchymal progenitor cells having surface antigen CD90, more than 95% of the allogeneic mesenchymal progenitor cells having surface antigen CD73, more than 95% of the allogeneic mesenchymal progenitor cells having surface antigen CD29, and more than 95% of the allogeneic mesenchymal progenitor cells having surface antigen CD49d;

said allogeneic interstitial vessel-layer cells have one or more features selected from the group consisting of more than 30% of the allogeneic interstitial vessel-layer cells having surface antigen CD29, more than 50% of the allogeneic interstitial vessel-layer cells having surface antigen CD73, more than 85% of the allogeneic interstitial vessel-layer cells having surface antigen CD49d, and more than 55% of the allogeneic interstitial vessel-layer cells having surface antigen CD90;

wherein the haMPCs are prepared by a method including:

digesting an adipose tissue by an enzyme to obtain stromal vascular fraction cells;

inoculating the stromal vascular fraction cells into a culture flask to obtain adherent cells;

culturing the adherent cells for 5-7 days to obtain primary adherent cells; and subjecting the primary adherent cells to passage at a ratio of 1:1-2 and culturing for 2-3 weeks.

2. The method of claim 1, wherein, said allogeneic interstitial vessel-layer cells have one or more features selected from the group consisting of more than 35% of the allogeneic interstitial vessel-layer cells having surface antigen CD29, more than 55% of the allogeneic interstitial vessel-layer cells having surface antigen CD73, more than 90% of the allogeneic interstitial vessel-layer cells having surface antigen CD49d, and more than 60% of the allogeneic interstitial vessel-layer cells having surface antigen CD90.

3. The method of claim 1, wherein said allogeneic interstitial vessel-layer cells have one or more features selected from the group consisting of less than 85% of the allogeneic interstitial vessel-layer cells having surface antigen CD34, and less than 15% of the allogeneic interstitial vessel-layer cells having surface antigen CD45.

4. The method of claim 1, wherein the allogeneic interstitial vessel-layer cells secrete one or more cytokines that are selected from the group consisting of stem cell growth factor (HGF), vascular endothelial growth factor (VEGF), platelet-derived growth factor (PDGF), transforming growth factor β (TGF-β), granulocyte-macrophage colony-stimulating factor (GM-CSF), interleukin-2 (IL-2), interleukin-10 (IL-10), and the combinations thereof.

5. The method of claim 1, wherein said allogeneic mesenchymal progenitor cells have one or more features selected from the group consisting of more than 98% of the allogeneic mesenchymal progenitor cells having surface antigen CD90, more than 98% of the allogeneic mesenchymal progenitor cells having surface antigen CD73, more than 98% of the allogeneic mesenchymal progenitor cells having surface antigen CD29, and more than 98% of the allogeneic mesenchymal progenitor cells having surface antigen CD49d.

6. The method of claim 1, wherein said allogeneic mesenchymal progenitor cells have one or more features selected from the group consisting of less than 2% of the allogeneic mesenchymal progenitor cells having surface antigen HLA-DR, less than 2% of the allogeneic mesenchymal progenitor cells having surface antigen Actin, less than 2% of the allogeneic mesenchymal progenitor cells having surface antigen CD34, less than 2% of the allogeneic mesenchymal progenitor cells having surface antigen CD45, and less than 2% of the allogeneic mesenchymal progenitor cells having surface antigen CD14.

7. The method of claim 1, wherein said allogeneic mesenchymal progenitor cells secrete one or more cytokines that are selected from the group consisting of vascular endothelial growth factor (VEGF), transforming growth factor α(TGF-α), transforming growth factor β (TGF-β), granulocyte-macrophage colony-stimulating factor (GM-CSF), hepatocyte growth factor (HGF), platelet-derived factor (PDGF), interleukin-2 (IL-2), interleukin-4 (IL-4), and interleukin-10 (IL-10).

8. A method for preventing and/or treating osteoarthritis comprising administering allogeneic interstitial vessel-layer cells (SVF) or a pharmaceutical composition thereof and administering allogeneic mesenchymal progenitor cells (haMPCs) or a pharmaceutical composition thereof to a subject in need thereof, wherein said allogeneic mesenchymal progenitor cells have one or more features selected from the group consisting of more than 95% of the allogeneic mesenchymal progenitor cells having surface antigen CD90;

more than 95% of the allogeneic mesenchymal progenitor cells having surface antigen CD73;

more than 95% of the allogeneic mesenchymal progenitor cells having surface antigen CD29;

more than 95% of the allogeneic mesenchymal progenitor cells having surface antigen CD49d;

said allogeneic interstitial vessel-layer cells have one or more features selected from the group consisting of more than 30% of the allogeneic interstitial vessel-layer cells having surface antigen CD29, more than 50% of the allogeneic interstitial vessel-layer cells having surface antigen CD73, more than 85% of the allogeneic interstitial vessel-layer cells having surface antigen CD49d, and more than 55% of the allogeneic interstitial vessel-layer cells having surface antigen CD90;

wherein the haMPCs are prepared by a method including:

digesting an adipose tissue by an enzyme to obtain stromal vascular fraction cells;

inoculating the stromal vascular fraction cells into a culture flask to obtain adherent cells;

culturing the adherent cells for 5-7 days to obtain primary adherent cells; and subjecting the primary adherent cells to passage at a ratio of 1:1-2 and culturing for 2-3 weeks.

9. A method for preventing and/or treating osteoarthritis comprising administering allogeneic mesenchymal progenitor cells (haMPCs) or a pharmaceutical composition comprising the haMPCs to a subject in need thereof,
wherein the haMPCs include more than 95% of the cells having surface antigen CD90, more than 95% of the cells having surface antigen CD73, more than 95% of the cells having surface antigen CD29, and more than 95% of the cells having surface antigen CD49d;
wherein the haMPCs are prepared by a method including:
digesting an adipose tissue by an enzyme to obtain stromal vascular fraction cells;
inoculating the stromal vascular fraction cells into a culture flask to obtain adherent cells;
culturing the adherent cells for 5-7 days to obtain primary adherent cells; and
subjecting the primary adherent cells to passage at a ratio of 1:1-2 and
culturing for 2-3 weeks.

* * * * *